(12) United States Patent
Yamada et al.

(10) Patent No.: US 10,733,734 B2
(45) Date of Patent: Aug. 4, 2020

(54) IMAGE ANALYSIS APPARATUS, IMAGE ANALYSIS SYSTEM, IMAGE ANALYSIS APPARATUS OPERATION METHOD TO ANALYZE BRIGHTNESS CHANGE OF SUBJECT

(71) Applicant: OLYMPUS CORPORATION, Tokyo (JP)

(72) Inventors: Tetsuhiro Yamada, Hino (JP); Momoko Yamanashi, Tachikawa (JP); Toshio Nakamura, Hachioji (JP); Ryuichi Toyama, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 220 days.

(21) Appl. No.: 15/671,567

(22) Filed: Aug. 8, 2017

(65) Prior Publication Data
US 2017/0337710 A1    Nov. 23, 2017

Related U.S. Application Data

(63) Continuation of application No. PCT/JP2016/062931, filed on Apr. 25, 2016.

(30) Foreign Application Priority Data

Apr. 27, 2015  (JP) ................................ 2015-090619

(51) Int. Cl.
*G06T 7/00*        (2017.01)
*A61B 1/00*        (2006.01)

(52) U.S. Cl.
CPC ........ *G06T 7/0016* (2013.01); *A61B 1/00009* (2013.01); *A61B 2576/00* (2013.01);
(Continued)

(58) Field of Classification Search
None
See application file for complete search history.

(56) References Cited

U.S. PATENT DOCUMENTS 5,699,798 A * 12/1997 Hochman ............ A61B 5/0059
                                                    600/420
2007/0276185 A1  11/2007 Gono et al.
2007/0292011 A1  12/2007 Nishimura et al.

FOREIGN PATENT DOCUMENTS

EP    1870020 A1    12/2007
EP    2022386 A1     2/2009
(Continued)

OTHER PUBLICATIONS

International Search Report dated Jun. 28, 2016 issued in PCT/JP2016/062931.
(Continued)

*Primary Examiner* — Justin P. Misleh
(74) *Attorney, Agent, or Firm* — Scully, Scott, Murphy & Presser, P.C.

(57) ABSTRACT

An image analysis apparatus includes a processor including hardware. The processor extracts parts from each of a first image and a second image acquired after the first image, each of the extracted parts including an annular peripheral portion and a central portion having a color different from a color of the peripheral portion. The processor also sets the central portion as the analysis object region and calculates a brightness decrease degree of the analysis object region in the second image relative to the analysis object region in the first image.

12 Claims, 7 Drawing Sheets

(52) U.S. Cl.
CPC .......... *G06T 2207/10068* (2013.01); *G06T 2207/30028* (2013.01)

(56) References Cited

FOREIGN PATENT DOCUMENTS

| | | |
|---|---|---|
| JP | 2006-288878 A | 10/2006 |
| JP | 2006-288879 A | 10/2006 |
| JP | 2007-502185 A | 2/2007 |
| JP | 2010-005056 A | 1/2010 |
| WO | WO 2006/112227 A1 | 10/2006 |
| WO | WO 2007/135757 A1 | 11/2007 |

OTHER PUBLICATIONS

Tanaka, M. et al., "Tokushu: Plus 30 Byo Shikisoho no Katsuyo Shocho Byohen: Shikiso Naishikyo no Katsuyo no Kihon to Kanbetsu Shindan", Endoscopia Digestiva, Dec. 25, 2006, pp. 1869-1878, vol. 18, No. 12.

Tanaka, M. et al., "Shocho Jumo no Keitai Bunrui", Endoscopia Digestiva, Jan. 25, 2014, pp. 75-80, vol. 26, No. 1.

\* cited by examiner

IMAGE ANALYSIS APPARATUS, IMAGE ANALYSIS SYSTEM, IMAGE ANALYSIS APPARATUS OPERATION METHOD TO ANALYZE BRIGHTNESS CHANGE OF SUBJECT

CROSS REFERENCE TO RELATED APPLICATION

This application is a continuation application of PCT/JP2016/062931 filed on Apr. 25, 2016 and claims benefit of Japanese Application No. 2015-090619 filed in Japan on Apr. 27, 2015, the entire contents of which are incorporated herein by this reference.

BACKGROUND OF THE INVENTION

1. Field of the Invention

The present invention relates to an image analysis apparatus, an image analysis system and an image analysis apparatus operation method that analyze a change of a subject from time-sequentially-acquired images of the subject.

2. Description of the Related Art

Various techniques of analyzing a change of a subject from time-sequentially-acquired images of the subject have conventionally been proposed.

For example, Japanese Patent Application Laid-Open Publication No. 2010-5056 describes a technique of an image acquisition apparatus that picks up a normal image of a subject to be observed, via an image pickup device and subjects an image signal outputted from the image pickup device to spectral image processing to generate a spectral estimation image signal having a predetermined wavelength, in which based on an image signal outputted from the image pickup device, a spectral estimation image signal having a particular wavelength relating to a drug dosed to a subject to be observed is generated as a spectral estimation image signal for luminance information acquisition in a spectral image generation section, each of pieces of luminance information in the spectral estimation image signals for luminance information acquisition, the spectral estimation image signals being generated at predetermined time intervals, is acquired in a luminance information acquisition section, a rate of change in the pieces of luminance information is acquired, and an image is displayed based on the rate of change in the pieces of luminance information on a display apparatus.

Also, Japanese Patent Application Laid-Open Publication No. 2007-502185 describes an image analysis method in which a digital image of a tissue of a tooth is picked up, for each of a plurality of pixels in the digital image, a first component value of a color of the pixel and a second component value of a color of the pixel are determined, and based on the first component value and the second component value, a first function value (for example, R/G) of the pixel is calculated.

SUMMARY OF THE INVENTION

An image analysis apparatus according to an aspect of the present invention includes: an image input section configured to receive an input of time-sequentially-acquired images of a subject; a region extraction section configured to set an analysis object region for each of a first image acquired at a first timing and a second image acquired at a second timing after the first timing, the first image and the second image being inputted from the image input section; and an image analysis section configured to calculate a brightness decrease degree of a part of the analysis object region in the second image, the part having a brightness decreased relative to the analysis object region in the first image.

An image analysis system according to an aspect of the present invention includes: an endoscope to be inserted into a subject to pick up and acquire an image of the subject; and the above-stated image analysis apparatus, and the image acquired by the endoscope is inputted to the image input section.

An image analysis apparatus operating method according to an aspect of the present invention includes: inputting time-sequentially-acquired images of a subject to an image input section; causing a region extraction section to set an analysis object region for each of a first image acquired at a first timing and a second image acquired at a second timing after the first timing, the first image and the second image being inputted from the image input section; and causing an image analysis section to calculate a brightness decrease degree of a part of the analysis object region in the second image, the part having a brightness decreased relative to the analysis object region in the first image.

DETAILED DESCRIPTION OF THE PREFERRED EMBODIMENTS

Embodiments of the present invention will be described below with reference to the drawings.

Embodiment 1

Figure 1:
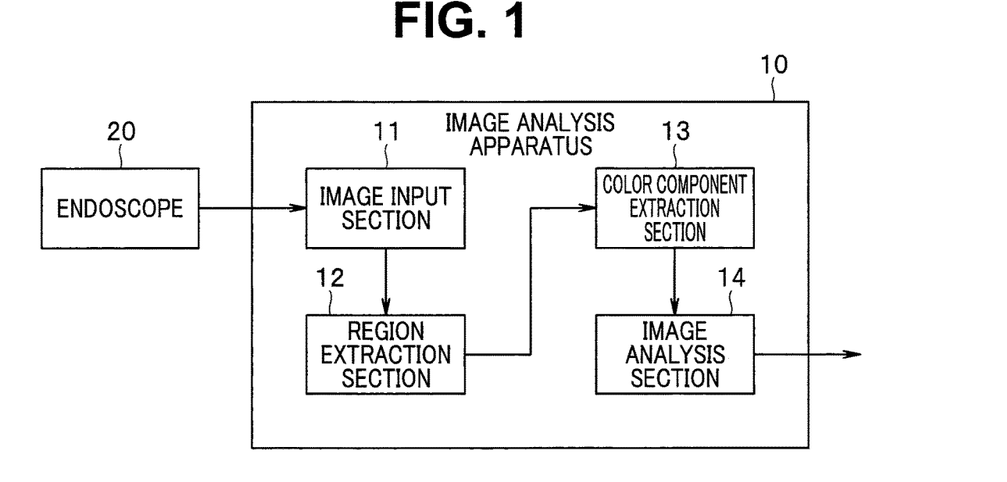
FIG. 1 is a block diagram illustrating a configuration of an image analysis system according to Embodiment 1 of the present invention.

FIGS. 1 to 9 indicate Embodiment 1 of the present invention, and FIG. 1 is a block diagram illustrating a configuration of an image analysis system.

The image analysis system includes an endoscope 20 and an image analysis apparatus 10.

The endoscope 20 is intended to be inserted into a subject to pick up and acquire an image of the subject, and in the present embodiment, enables, for example, narrow-band observation (narrow band imaging: NBI). Here, for NBI enlarged observation with noise components reduced, for example, a distal end hood or a distal end attachment is fitted to a distal end of the endoscope 20. In the present embodiment, a load is placed to a subject, and in order to observe a change of the subject between before and after placing the load, images of the subject are acquired time-sequentially by the endoscope 20. Also, in order to more precisely capture the change of the subject between before and after charging the load, it is desirable that a brightness of the endoscope 20 be set in a same condition. Therefore, it is favorable to acquire the images of the subject with a constant amount of light emitted from a light source with no light adjustment performed in the light source before and after placing the load to the subject.

The image analysis apparatus 10 includes an image input section 11, a region extraction section 12, a color component extraction section 13 and an image analysis section 14.

The image input section 11 receives an input of images of a subject, the images being time-sequentially acquired by the endoscope 20.

The region extraction section 12 sets elements, which are one part or parts of a predetermined plural number (as described later, elements in the present embodiment are, for example, central portions of image parts of villi of an intestinal tract) as an analysis object region, for each of a first image acquired at a first timing and a second image acquired at a second timing after the first timing, the first image and the second image being inputted from the image input section 11. Therefore, an analysis object region is set as a region including one element or a predetermined number of elements.

The color component extraction section 13 extracts color component values of each of the elements included in the set analysis object region.

The image analysis section 14 calculates a degree of change based only on a color component value, the color component value of the second image being lower than the color component value of the first image, of the color component values extracted from the analysis object region.

Figure 2:
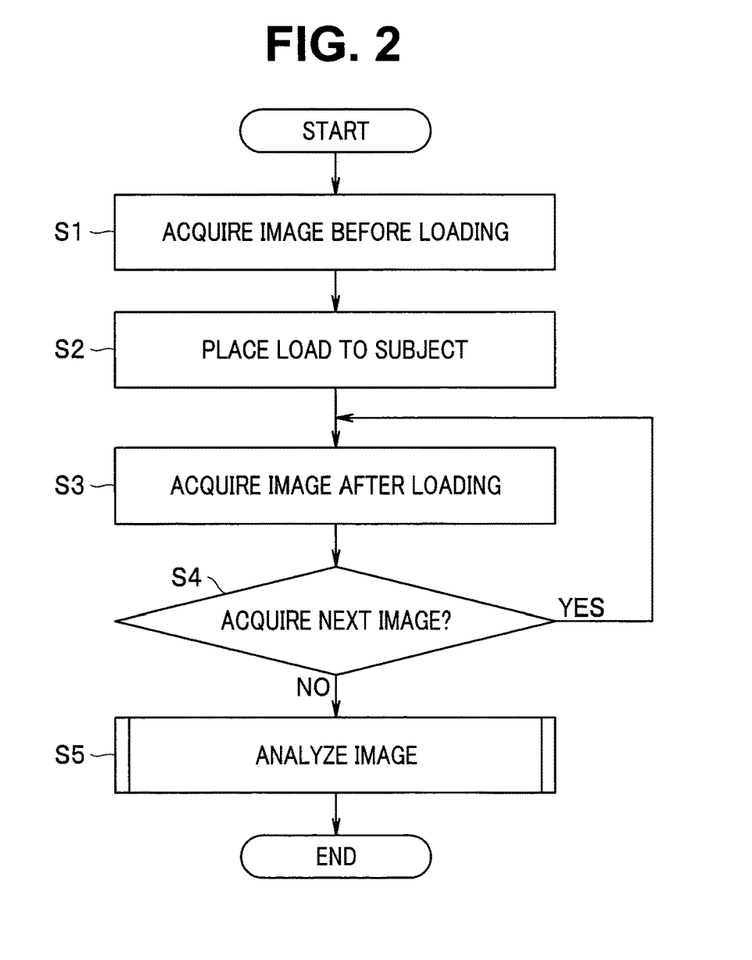
FIG. 2 is a flowchart indicating processing using the image analysis system according to Embodiment 1 above.

Next, FIG. 2 is a flowchart indicating processing using the image analysis system.

For example, it is known that if a load is provided to a subject that is a normal living tissue such as villi of an intestinal tract (further, for example, a small intestine), a blood flow increases and consequently a brightness of an image capturing the living tissue changes to be dark. Analysis of image brightness change between before and after stimulating the living tissue using this characteristic is performed to determine whether the living tissue is normal or abnormal (lesion) (however, the subject is not limited to this example and other examples of the subject include, e.g., a tongue part, an esophagus, a gastric mucosa and a large intestine).

Upon a start of this processing, an image before placing a load to a subject (image before loading or first image) is picked up at a first timing by the endoscope 20 (step S1).

Also, simultaneously with acquisition of the image of the subject by the endoscope 20, information on an amount of light emitted at the time of the image acquisition may be recorded in, for example, the image analysis apparatus 10 or the endoscope 20.

Subsequently, a load is provided to the subject (step S2). Here, for example, glucose is dispersed as a load (however, the load is not limited to this example, and an intravenous injection may be performed or another load may be provided). The glucose dispersion causes an increase in amount of blood flowing in the capillaries and light is absorbed more by hemoglobin in the blood. Therefore, a part in the villi in which capillaries gather is observed as being dark.

Subsequently, at a second timing after the aforementioned first timing, an image after placing the load (image after loading or second image) is picked up and acquired by the endoscope 20 (step S3). When the image after placing the load to the subject is acquired by the endoscope 20, if the emitted light amount information is recorded in step S1, the image is acquired on a condition that is the same as the condition in step S1 with reference to the emitted light amount information. Also, a function that deletes the emitted light amount information recorded in step S1 later may be provided, and the acquisition of the emitted light amount information, the image acquisition using the emitted light amount information and the deletion of the emitted light amount information may be performed by operation of, for example, an operation portion of the endoscope 20, a switch provided on a control panel for controlling the image analysis system or a foot switch for operating the endoscope 20.

Then, whether or not a next image is further acquired is determined (step S4), and if it is determined that a next image is further acquired, the processing returns to step S3 and a next image after loading is acquired.

Also, in step S4, if it is determined that the acquisition of the image is finished, the analysis of the image is performed by the image analysis apparatus 10 (step S5), and upon completion of the image analysis, this processing ends.

Figure 3:
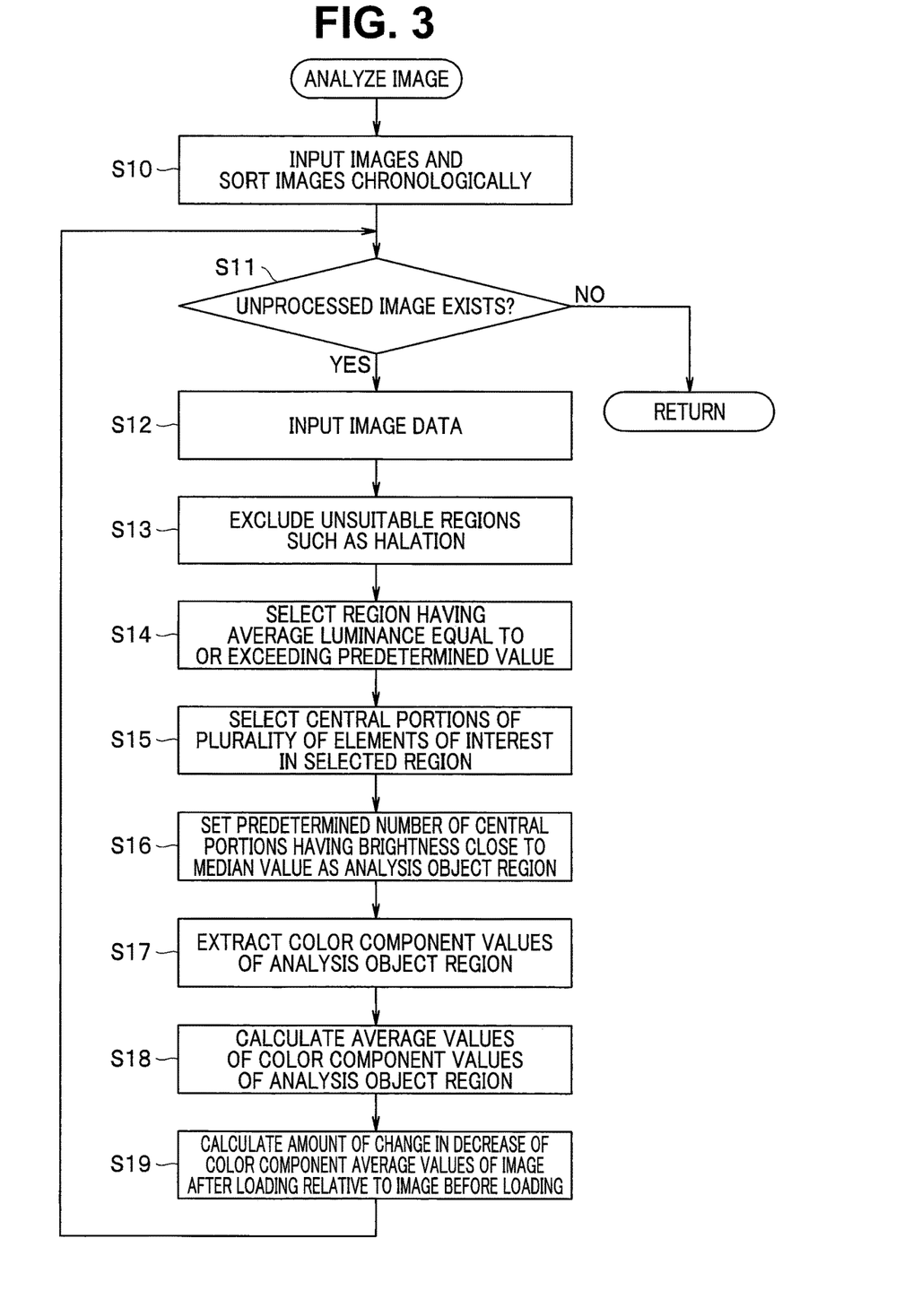
FIG. 3 is a flowchart indicating image analysis processing performed by an image analysis apparatus according to Embodiment 1 above.

FIG. 3 is a flowchart indicating image analysis processing performed by the image analysis apparatus 10.

Upon a start of this processing, the image input section 11 receives an input of time-sequentially-acquired images of a subject from the endoscope 20 and sorts the images chronologically (step S10).

Figure 4:
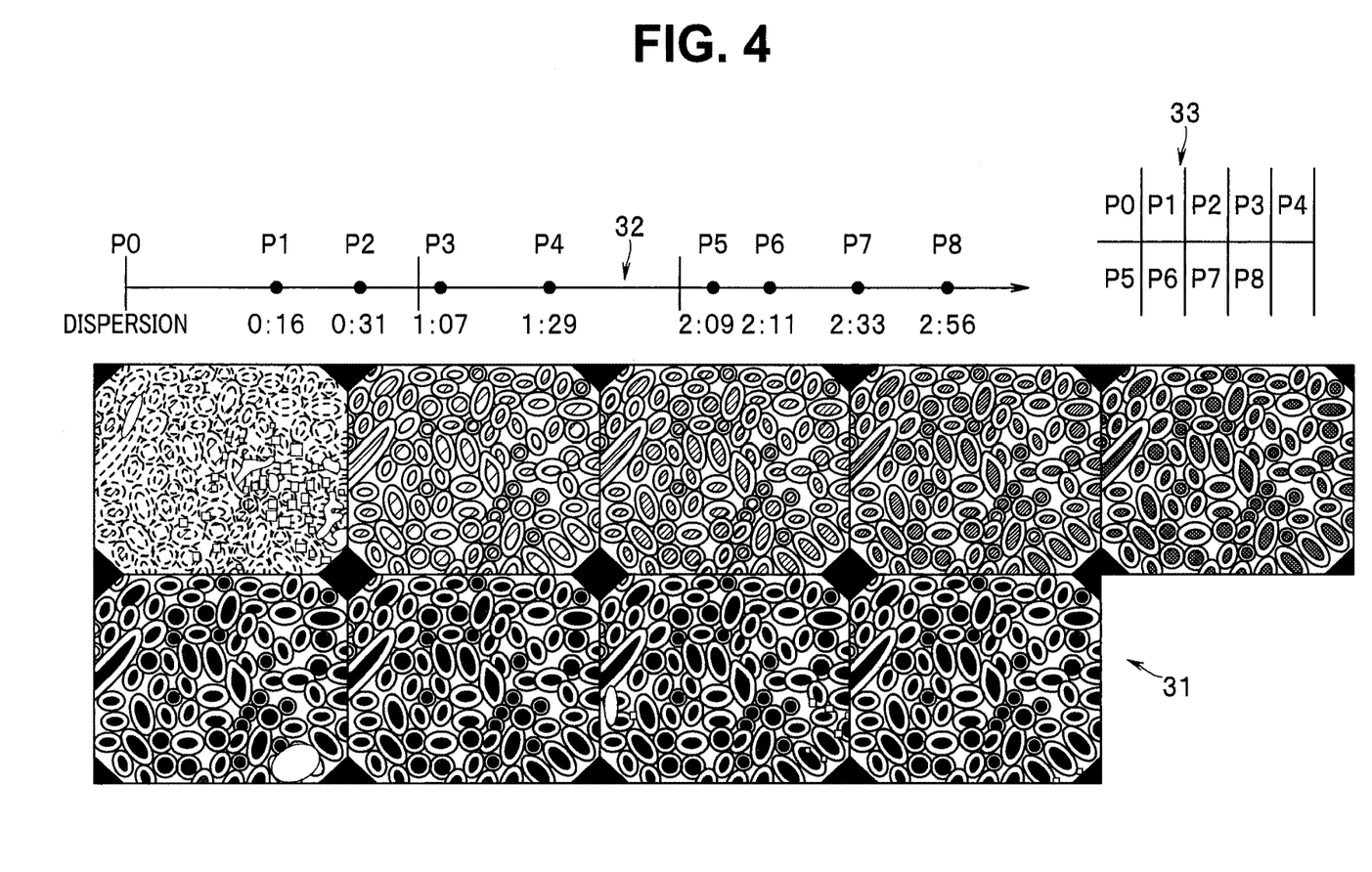
FIG. 4 is a diagram illustrating a display example of chronologically-sorted images of a subject in Embodiment 1 above.

FIG. 4 is a diagram illustrating a display example of chronologically-sorted images of a subject.

In the display example illustrated in FIG. 4, image sequence display 31, image acquisition time display 32 and image sequential order display 33 are provided on a display apparatus such as a monitor.

First, in the image sequence display 31, acquired images P0 to P8 of a subject are displayed in a sequence in order of time of the acquisition.

Also, the image acquisition time display 32 indicates a point of time of acquisition of each of the images P1 to P8 after placing a load (dispersion of glucose), for example, along a time axis together with a time of the acquisition. Although the image P0 is an image acquired before the glucose dispersion (for example, immediately before the glucose dispersion), in the example illustrated in FIG. 4, for sake of convenience, the image P0 is indicated at a position of the glucose dispersion (However, it should be understood that the time axis may be extended to a point of time before the dispersion to correctly indicate the point of time of the acquisition of the image P0).

Furthermore, the image sequential order display 33 indicates correspondence between each image included in the image sequence display 31 and a point of time of the acquisition of the image from among the images P0 to P8 indicated in the image acquisition time display 32.

Next, the image analysis apparatus 10 determines whether or not an image not yet subjected to processing that will be described later with reference to steps S12 to S19 exists (step S11).

Here, if it is determined that an image not yet subjected to the processing exists, the region extraction section 12 receives an input of image data that is a processing object from the image input section 11 (step S12).

Then, regions (unsuitable regions) IR of unsuitable elements (unsuitable parts), such as halation, that are unsuitable for extraction of brightness component values (for example, color component values) (see, e.g., FIGS. 5 and 6) are excluded from the processing object (step S13). Here, examples of the unsuitable regions IR include, a region in which air bubbles are generated and a blurred region other than a region in which halation occurs.

Furthermore, a region having an average luminance that is equal to or exceeds a predetermined value, the average luminance being calculated for each of partial regions each having a predetermined size, in the image is selected as a proper luminance region (step S14). For example, in an image Pi (here, i is any of 0 to 8 in the example illustrated in FIG. 4 (that is, Pi is any of P0 to P8)) illustrated in FIG. 5 (or FIG. 6), an average luminance of the upper right half region is lower than the predetermined value. Here, FIG. 5 includes a diagram illustrating a brightness distribution in an image of a subject and an enlarged view of one of elements of interest (parts of interest).

Figure 7:
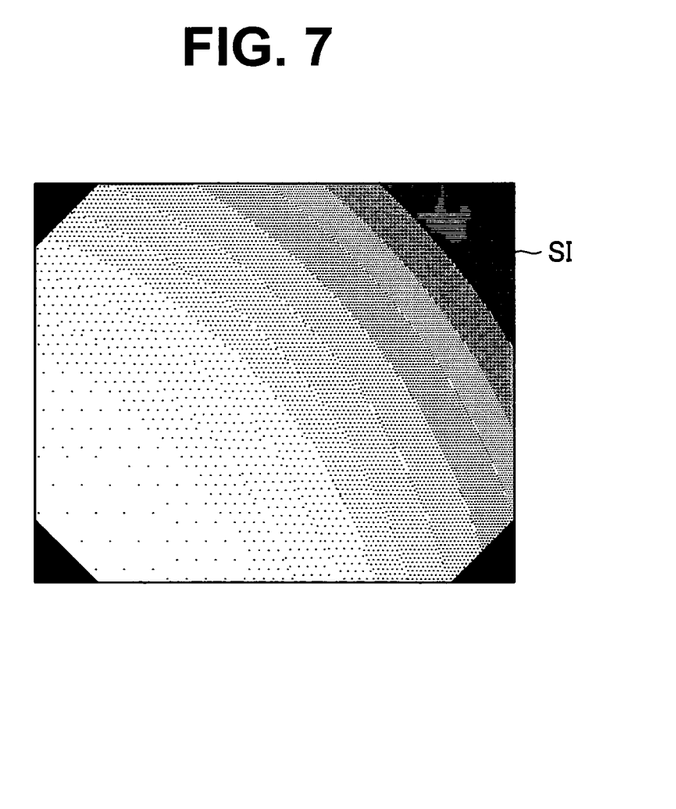
FIG. 7 is a diagram illustrating an example of an endoscope brightness simulation result in Embodiment 1 above.
Figure 8:
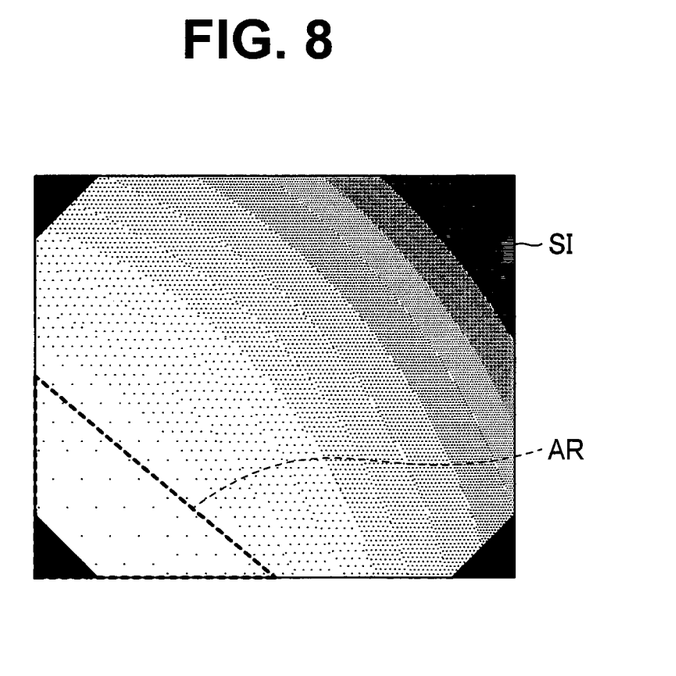
FIG. 8 is a diagram illustrating an example of a region that is suitable for color component value extraction, the region being obtained from the endoscope brightness simulation result, in Embodiment 1 above.

Although in the above description, an analysis object region is set using an image of a subject acquired by, e.g., the endoscope 20 as an image indicating performance of an image pickup apparatus configured to pick up an image to be inputted from the image input section 11, the method of setting an analysis object rejoin is not limited to this method, and a method in which with reference to average luminances calculated for respective partial regions each having a predetermined size based on another image indicating performance of the image pickup apparatus (for example, an image taken of a flat object having an even color such as a test plate or a white balance cap or an image that provides an indication of performance such as a brightness simulation result SI (see FIG. 7) obtained from design values of the endoscope 20), a region AR (see FIG. 8) that is suitable for color component value extraction is set as an analysis object region may be employed. Furthermore, a method in which an analysis object region is set in the region AR that is suitable for color component value extraction, based on the average luminances calculated for the respective partial regions each having a predetermined size may be employed. Here, FIG. 7 is a diagram illustrating an example of a brightness simulation result SI for the endoscope 20, and FIG. 8 is a diagram illustrating an example of a region AR that is suitable for extraction of color component values obtained from the brightness simulation result SI for the endoscope 20.

Figure 5:
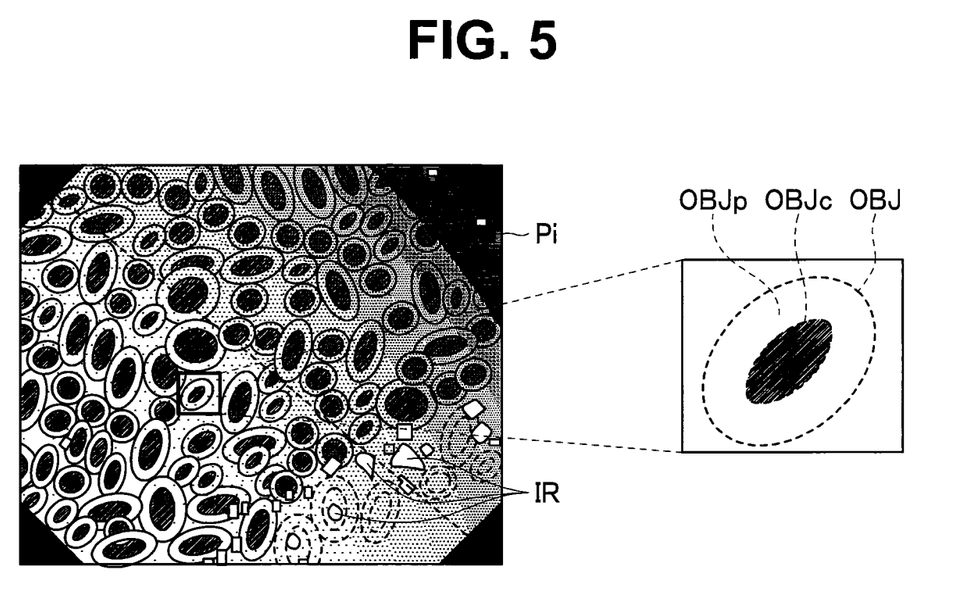
FIG. 5 includes a diagram illustrating a brightness distribution in an image of a subject and an enlarged view of one of elements of interest in Embodiment 1 above.
Figure 6:
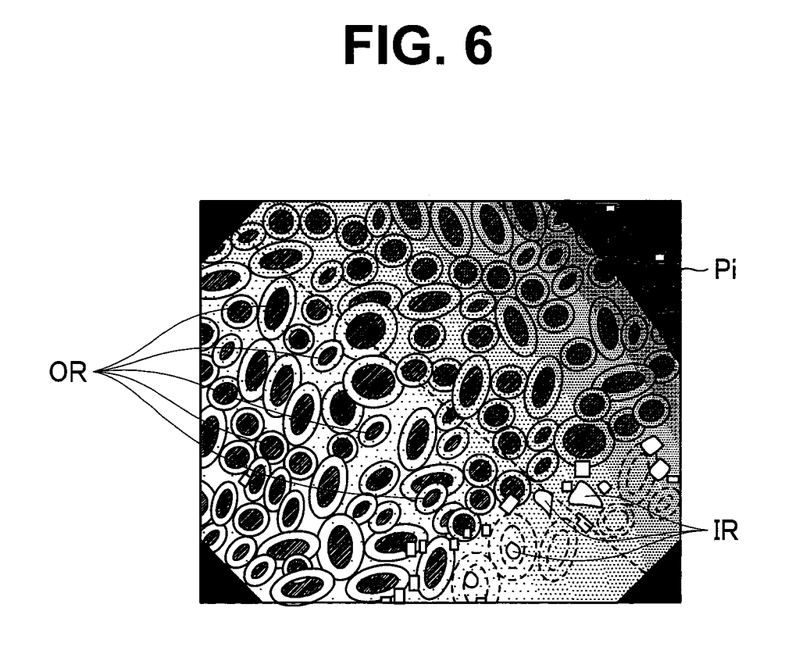
FIG. 6 is a diagram illustrating an example of an analysis object region set in the image of the subject in Embodiment 1 above.

Returning to the description of the example illustrated in FIGS. 5 and 6, the region extraction section 12 selects a lower left half region of the image Pi, the region having an average luminance that is equal to or exceeds the predetermined value as a proper luminance region. Such selection allows selection of a bright region that is suitable for color component value extraction and exclusion of a dark region that is not suitable for color component value extraction.

Although, here, a proper luminance range that is suitable for color component value extraction is a range having an average luminance that is equal to or exceeds the predetermined value, an excessively-bright region having an average luminance close to a saturated pixel value may be excluded. In this case, a proper luminance range that is suitable for color component value extraction is set as a range having an average luminance that is equal to or exceeds a predetermined lower limit threshold value and is equal to or below a predetermined upper limit threshold value.

If a scale of luminance in an image has, for example, 256 levels of 0 to 255, a proper luminance range including, for example, 10 corresponding to a frame part of an endoscopic image as a lower limit threshold value and, for example, 230 corresponding to halation as an upper limit threshold value is set, enabling extraction of color components of an analysis object alone and thus enabling enhancement in analysis precision.

Subsequently, in the selected region, a central portion OBJc (this central portion OBJc is also an element) of each of a plurality of elements of interest (parts of interest) (image parts of villi of an intestinal tract in the present embodiment) OBJ is selected (step S15).

First, a plurality of image parts of villi of an intestinal tract, which are elements of interest OBJ, may manually be selected by a user viewing the image or, e.g., image analysis or the like may be performed to extract and select a plurality of elements of interest OBJ by means of automatic processing. Here, an image part of a villus of an intestinal tract, which is an element of interest OBJ, is an element including a peripheral portion OBJp having an annular shape (not limited to a circular ring shape and may be an arbitrary closed curve shape), and a central portion OBJc surrounded by the peripheral portion OBJp and having a color that is different from a color of the peripheral portion OBJp. The peripheral portion OBJp is an image part in which mucosal epithelium formed on a surface of the villus of the intestinal tract is shown as an annular peripheral portion. Also, the central portion OBJc is an image part in which a site surrounded by the mucosal epithelium is shown as a central portion having a color that is different from a color of the mucosal epithelium.

Therefore, upon selection of the plurality of elements of interest OBJ, central portions OBJc of the selected elements of interest OBJ are further selected respectively based on the color difference (this selection can also be performed either manually or automatically).

Furthermore, from among the plurality of selected central portions OBJc, a predetermined number of (five in the example illustrated in FIG. 6) the central portions OBJc each having a brightness close to a median value are further selected, and the predetermined number of central portions OBJc selected are set as an analysis object region OR (step S16). Here, FIG. 6 is a diagram illustrating an example of an analysis object region OR set in an image Pi of a subject.

Here, the selection of the central portions OBJc each having a brightness close to the median value is intended to obtain analysis objects each having a brightness that is most suitable for samples. Here, for the brightness, a luminance value obtained by, for example, performing an arithmetic operation such as indicated in Equation 4, which will be indicated later, based on a plurality of color components may be used or a value obtained by simply adding up a plurality of color components may be used instead as an index of brightness, or the brightness may be acquired based on a plurality of color components by means of another method. As described above, the analysis object region OR illustrated in FIG. 6, which are set here, includes, for example, five central portions OBJc, which are image parts of villi of an intestinal tract.

Next, the color component extraction section 13 extracts color component values, for example, an R component value, a G component value and a B component value, of each pixel included in the analysis object region OR (step S17), and calculates an average value <R> of the R component values, an average value <G> of the G component values and an average value <B> of the B component values in the analysis object region OR (step S18).

Then, the image analysis section 14 calculates an amount of change in decrease of the color component average values as a degree of change of the image after loading relative to the image before loading (step S19).

More specifically, it is assumed that <R>, <G> and <B> are the average values of the respective R (red), G (green) and B (blue) component values in the analysis object region OR in the image before loading and <R'>, <G'> and <B'> are the average values of the respective R, G and B component values in the analysis object region OR in the image after loading. Furthermore, it is assumed that Min(x, y) is a function that outputs one that is not larger of x and y (where x≠y, a smaller one).

In this case, the image analysis section 14 calculates, for example, a change amount that is made to be an absolute value such as indicated in Equation 1 below (however, making a change amount be an absolute value is not essential and thus it is possible not to make a change amount be an absolute value).

$$\text{Change amount} = |\text{Min}(<R'> - <R>, 0) + \text{Min}(<G'> - <G>, 0) + \text{Min}(<B'> - <B>, 0)|$$ [Equation 1]

Therefore, if a result of subtraction of an average value of an arbitrary color component of R, G or B in the image before loading from an average value of the color component of the image after loading is negative, such result contributes to the change amount, but if the subtraction result is positive, such result does not contribute to the change amount (because 0 is outputted from the function Min). As a result of such arithmetic operation being performed, the amount of change in decrease of the color component average values is calculated.

Figure 9:
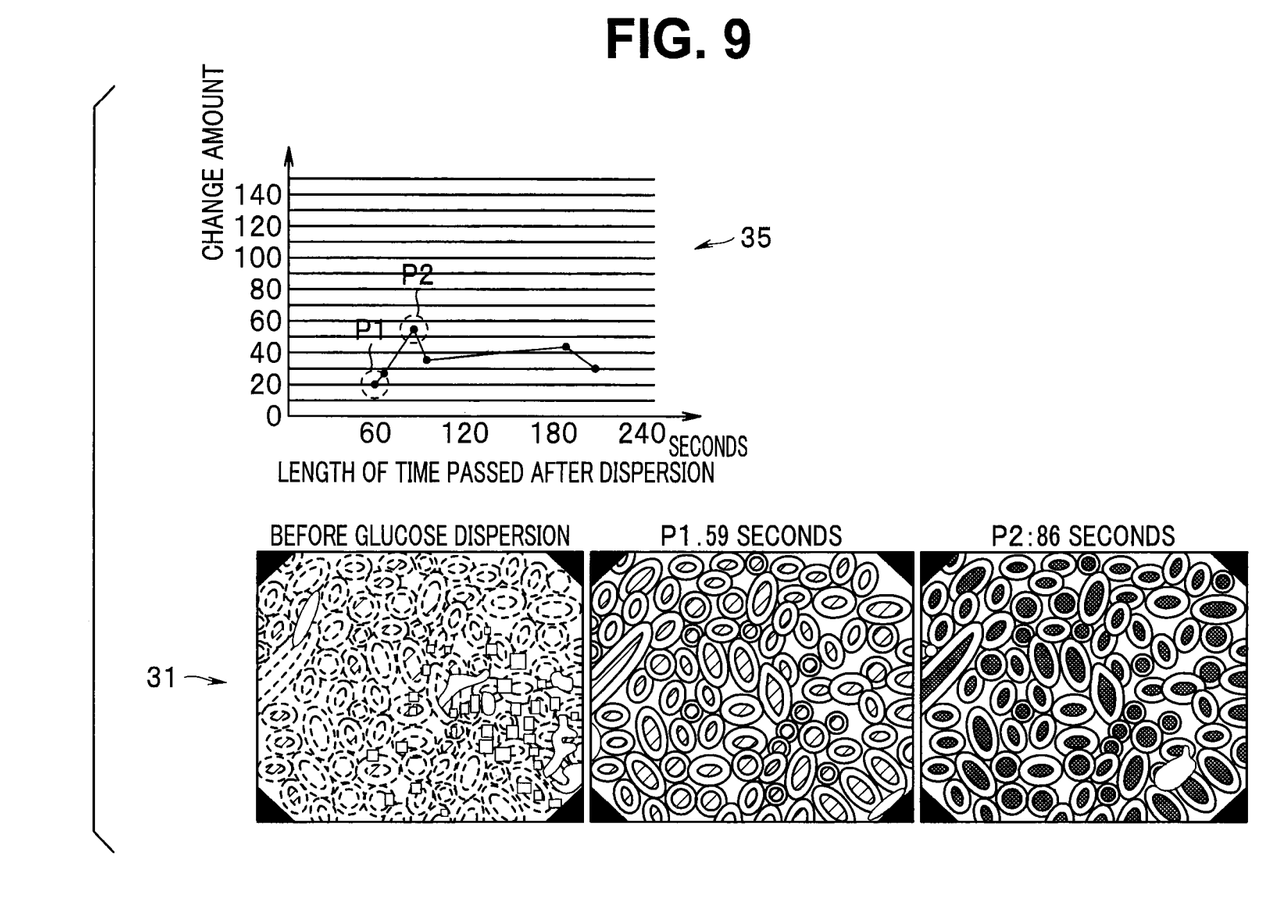
FIG. 9 is a diagram illustrating an example in which chronologically-sorted images of a subject are displayed together with amounts of change of the images in Embodiment 1 above.

The change amounts calculated as above are, for example, as illustrated in FIG. 9, displayed together with the images. FIG. 9 is a diagram illustrating an example in which chronologically-sorted images of a subject are displayed together with amounts of change of the images.

In the display example illustrated in FIG. 9, change amount display 35 is provided together with image sequence display 31. The change amount display 35 is a graph indicating transition of the amount of change in the images after loading relative to the image before loading, and the vertical axis represents change amount, and the horizontal axis represents a length of time passed after glucose dispersion.

After step S19 is performed, the processing returns to step S11 described above. Then, if it is determined in step S11 that processing for all of the images has been performed, the operation returns from this processing to non-illustrated main processing.

Not only blood vessels but also other tissues are included in an analysis object region. The blood vessel parts change to be darker upon an increase in amount of blood. Thus, when the above-described analysis is performed, a part including no blood vessel may vary to be brighter.

Variation of an image to be brighter causes noise in the above-described analysis, and thus, for enhancement in precision of the analysis, it is necessary to enable analysis with such noise removed.

According to Embodiment 1 as above, a degree of brightness decrease in a part of an analysis object region in a second image, the part having a brightness decreased relative to a brightness of an analysis object region in a first image, is calculated (for example, a degree of change is calculated based only on a color component value, the color component value of the second image being lower than the color component value of the first image, of the color component values extracted from the color analysis object region), enabling obtainment of a highly-precise result as a result of image analysis where a brightness of an image of a subject such as a living tissue changes from the bright side to the dark side.

Then, a predetermined number of elements (parts) each including an annular peripheral portion and a central portion surrounded by the peripheral portion and having a color that is different from a color of the peripheral portion are extracted and the respective central portions of the predetermined number of elements (parts) extracted are set as an analysis object region, enabling, for example, image parts of villi of an intestinal tract to be set as analysis objects.

Also, when an analysis object region is set, unsuitable elements (unsuitable parts) that are not suitable for brightness component value (for example, color component value) extraction are excluded, enabling obtainment of more accurate image analysis result that is not affected by the unsuitable elements (unsuitable parts).

Furthermore, an analysis object region is set in a proper luminance region having an average luminance in a proper luminance range that is suitable for color component value extraction, and thus, an excessively-bright region or an excessively-dark region in which even if a subject changes, the amount of the change is not necessarily properly reflected in pixel values can be prevented from being set as an analysis object region.

In addition, a predetermined number of elements (parts) each having a brightness close to a median value is set as an analysis object region, enabling more proper capturing of a change amount.

Then, since a change amount is calculated as indicated in Equation 1, and thus, it is only necessary to perform simple arithmetic processing such as addition/subtraction, comparison and an absolute value, enabling an increase in speed of the processing.

Also, the aforementioned effects can be exerted for images of a subject acquired by the endoscope 20.

Furthermore, for example, proper image analysis can be performed for villi of an intestinal tract.

Note that what is set as an analysis object region in a selected region is not limited to a plurality of elements of interest (parts of interest) and may be a single element of interest (part of interest) as long as the element of interest (part of interest) is not one unsuitable for luminance detection.

Embodiment 2

Figure 10:
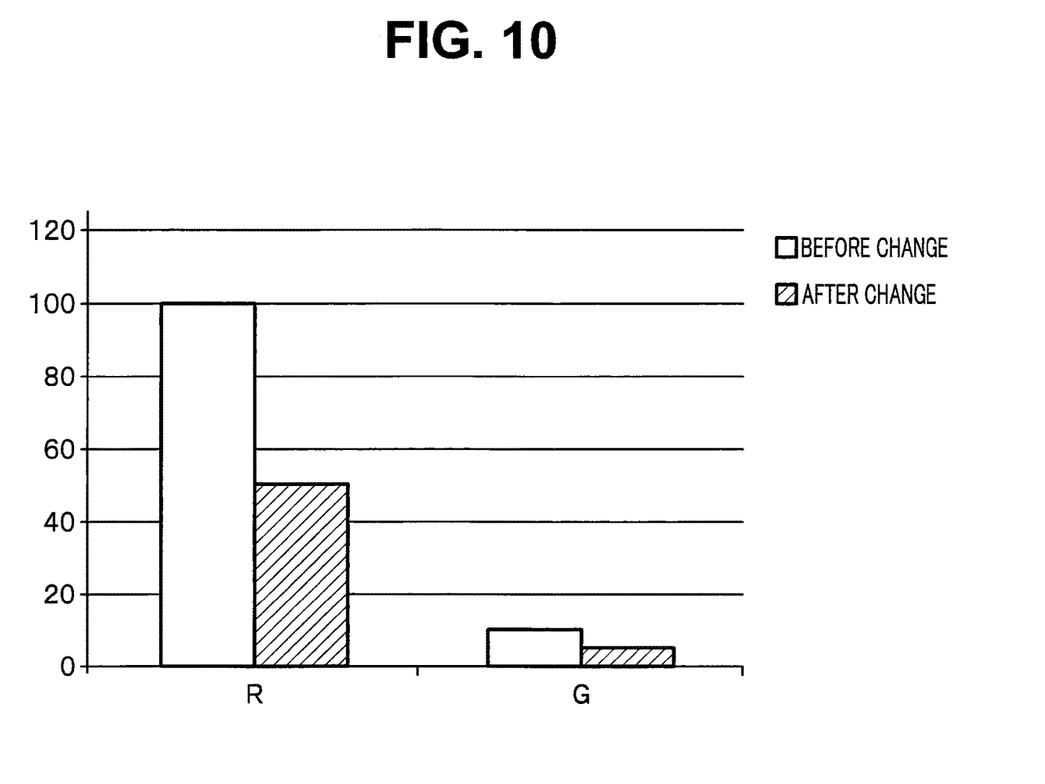
FIG. 10 is a graph for describing that where signal values of color components are different from one another, a change amount differs even if a change ratio is the same in Embodiment 2 of the present invention.

FIG. 10 indicates Embodiment 2 of the present invention and is a graph for describing that where signal values of color components are different from one another, a change amount differs even if a change ratio is the same.

In Embodiment 2, description of parts that are similar to the parts in Embodiment 1 described above will arbitrarily be omitted by, e.g. providing reference numerals that are the same as the reference numerals in Embodiment 1 to the parts, and the description will be provided mainly on differences.

In Embodiment 1 described above, as indicated in Equation 1, a color component, an average value of which has been reduced in an image after loading relative to an image before loading, contributes to a change amount calculated, by the amount of the reduction.

However, such processing causes the following.

For example, as indicated in FIG. 10, it is assumed that an R component average value is 100 and a G component average value is 10 in an image before loading. Then, it is assumed that signal values of an image after loading have been reduced to half relative to signal values of the image before loading.

In this case, respective change ratios of the R component average value and the G component average value are both 50% and thus equal to each other; however, while the R component average value of 50 contributes to the change amount indicated in Equation 1, the G component average value of 5 contributes to the change amount.

The present embodiment enables control of an amount of contribution to a change amount according to a magnitude of a color component average value.

In other words, in the present embodiment, a change amount is calculated as indicated in Equation 2 below using weight coefficients α, β and γ (here, α>0, β>0, γ>0) for respective color components.

Change amount = [Equation 2]

$$|\alpha \times \text{Min}(<R'> - <R>, 0) + \beta \times \text{Min}(<G'> - <G>, 0) + \gamma \times \text{Min}(<B'> - <B>, 0)|$$

Then, adjustment of weight coefficients α, β and γ in Equation 2 enables control of how much each color component average value contributes to the change amount.

Here, in Equation 2, if α=β=γ=1, a change amount that is similar to a change amount in Embodiment 1 described above can be obtained.

According to Embodiment 2, effects that are substantially similar to the effects of Embodiment 1 described above are exerted, and when a change amount is calculated, an amount of contribution of each color component average value to the change amount can be controlled in a desired manner because the change amount is calculated based on Equation 2.

Therefore, for example, a change amount can be calculated with attention focused on a particular color component of respective R, G and B components.

Also, a change amount can be calculated in consideration of, e.g., a hue of a subject, for example, a subject being a subject that is rich in red color component.

Embodiment 3

Next, Embodiment 3 of the present invention will be described.

In Embodiment 3, description of parts that are similar to the parts in Embodiments 1 and 2 described above will arbitrarily be omitted by, e.g., providing reference numerals that are the same as the reference numerals in Embodiments 1 and 2 to the parts, and the description will be provided mainly on differences.

In Embodiments 1 and 2 described above, a change amount is calculated. However, in these cases, as will be described below, comparison between calculated change amounts may be difficult.

First, if image pickup conditions (e.g., an exposure time period, an aperture value and/or an illuminance of a subject) for respective images in a series of images time-sequentially acquired (image before loading and images after loading) are equal to one another, comparison between change amounts in the series of images, for example, comparison between a first change amount of an image P1 after loading relative to an image P0 before loading and an second change amount of an image P2 after loading relative to the image P0 before loading is possible.

However, in the case of a plurality of groups of images picked up on different conditions, generally, change amounts sometimes cannot be compared directly because of a difference in brightness between the images. For example, even though a group of images taken of a certain subject and a group of images taken of another subject are compared in terms of change amount, where a brightness of one of the image groups is twice a brightness of the other image group, a calculated change amount of the one image group is twice a calculated change amount of the other image group even if pathological change amounts are the same.

Therefore, in the present embodiment, change rates are calculated instead of change amounts to enable comparison in such cases.

In other words, in the present embodiment, as indicated in Equation 3 below, a change rate is calculated by dividing a change amount by an absolute value of a value of addition of respective color component average values of an image before loading.

Change rate = [Equation 3]

$$|\alpha \times \text{Min}(<R'> - <R>, 0) + \beta \times \text{Min}(<G'> - <G>, 0) + \gamma \times \text{Min}(<B'> - <B>, 0)| / |<R> + <G> + <B>|$$

Here, Equation 3 provides a change rate for a change amount in Embodiment 2 above in which weight coefficients α, β and γ are used, but where α=β=γ=1, a change rate for a change amount in Embodiment 1 described above can be obtained.

Also, here, a change rate is calculated by dividing a change amount by an absolute value |<R>+<G>+<B>| of a value of addition of respective color component average values, but a change rate may be calculated by calculating a luminance average value <Y> of an image before loading from respective color component average values <R>, <G> and <B>, for example, as indicated in Equation 4 below, $$<Y> = 0.299 \times <R> + 0.587 \times <G> + 0.114 \times <B>$$ [Equation 4]

and dividing a change amount indicated in Equation 2 by an absolute value |<Y>| of the luminance average value calculated according to Equation 4. Here, although general luminance calculation coefficients (0.299, 0.587 and 0.114) are used, if elements of a color on which attention is to be focused from among respective color components of R, G and B are more properly shown with emphasis, the values of the coefficients by which the respective color components of R, G and B are multiplied may be changed to values that are different from the above values.

Furthermore, an amount of light emitted from a light source of an endoscope 20 may be extracted from, for example, a degree of opening of a diaphragm of the light source and values of the amount of light may be set as respective coefficient values of α, β and γ so that an impact of a difference in amount of light emitted from the light source on images can be reduced.

According to Embodiment 3 as above, effects that are substantially similar to the effects of Embodiments 1 and 2 described above, and a change rate is calculated instead of a change amount, enabling comparison between change rates calculated from image groups having different brightnesses.

Note that each of the above-described sections may be configured as a circuit. Any circuit may be implemented as a single circuit or may be implemented as a combination of a plurality of circuits as long as the circuit can fulfill a same function. Furthermore, any circuit is not limited to one configured as a dedicated circuit for fulfilling an intended function and may be one configured to fulfill an intended function by causing a general-purpose circuit to execute a processing program.

Also, although the above description have been provided mainly on an image analysis apparatus (or an image analysis system; the same applies hereafter), the present invention may be of, for example, an operation method for causing the image analysis apparatus to operate in such a manner as described above, a processing program for causing a computer to perform processing that is similar to processing performed by the image analysis apparatus or a non-temporary recording medium that can be read by a computer with the processing program recorded.

Furthermore, the present invention is not limited to the above-described embodiments as they are, and in the practical phase, can be embodied with components modified without departing from the spirit of the invention. Also, each of various aspects of the invention can be formed by an arbitrary combination of a plurality of components disclosed in the above embodiments. For example, some components may be deleted from all the components indicated in an embodiment. Furthermore, components in different embodiments may arbitrarily be combined. As described above, it should be understood that various modifications and applications are possible without departing from the spirit of the invention.

What is claimed is:

1. An image analysis apparatus comprising a processor comprising hardware, wherein the processor is configured to:
   receive, at the processor, an input of time-sequentially-acquired images of a subject, the time-sequentially-acquired images including a first image acquired at a first time and a second image acquired at a second time after the first time;
   extract first parts from the first image, each of the extracted first parts including a first annular peripheral portion and a first central portion surrounded by the first annular peripheral portion, the first central portion having a first color that is different from a second color of the first annular peripheral portion;
   extract second parts from the second image, each of the extracted second parts including a second annular peripheral portion and a second central portion surrounded by the second annular peripheral portion, the second central portion having a third color that is different from a fourth color of the second annular peripheral portion;
   set the first central portion of each of the extracted first parts as a first analysis object region;
   set the second central portion of each of the extracted second parts as a second analysis object region; and
   calculate a brightness decrease degree of the second analysis object region relative to the first analysis object region, the second analysis object region having a brightness decreased relative to the first analysis object region.

2. The image analysis apparatus according to claim 1, wherein the first time is a time before a load is placed to the subject, and the second time is a time after the first time and after the load is placed to the subject.

3. The image analysis apparatus according to claim 1, wherein the processor is configured to:
   exclude, from the first image, a first unsuitable part that is unsuitable for brightness component value extraction to set the first analysis object region; and
   exclude, from the second image, a second unsuitable part that is unsuitable for brightness component value extraction to set the second analysis object region.

4. The image analysis apparatus according to claim 1, wherein the processor is configured to:
   extract color component values in the set first analysis object region,
   extract color component values in the set second analysis object region; and
   calculate a brightness change degree based only on a color component value, the color component value being such that the color component values extracted from the second analysis object region are lower than the color component values extracted from the first analysis object region.

5. The image analysis apparatus according to claim 4, wherein the processor is configured to:
   set a plurality of partial regions each having a predetermined size in an image indicating performance of an image pickup apparatus configured to acquire an image to be inputted to the processor;
   calculate an average luminance for each partial region of the plurality of partial regions; and
   set the first analysis object region and the second analysis object region within a proper luminance region comprising one or more of the partial regions in which the average luminance is within a luminance range that permits color component value extraction.

6. The image analysis apparatus according to claim 4, wherein where <R>, <G> and <B> are respective average values of R, G and B components in the first analysis object region, <R'>, <G'> and <B'> are respective average values of R, G and B components in the second analysis object region and Min(x, y) is a function that provides one that is not larger of x and y, and the processor is configured to calculate the change degree as the following change amount:

$$\text{Change amount} = |\text{Min}(<R'> - <R>, 0) + \text{Min}(<G'> - <G>, 0) + \text{Min}(<B'> - <B>, 0)|.$$

7. The image analysis apparatus according to claim 4, wherein where <R>, <G> and <B> are respective average values of R, G and B components in the first analysis object region, <R'>, <G'> and <B'> are respective average values of R, G and B components in the second analysis object region, Min(x, y) is a function that provides one that is not larger of x and y and α, β and γ(here, α>0, β>0, γ>0) are weight coefficients, and the processor is configured to calculate the change degree as the following change amount:

$$\text{Change amount} = |\alpha \times \text{Min}(<R'> - <R>, 0) + \beta \times \text{Min}(<G'> - <G>, 0) + \gamma \times \text{Min}(<B'> - <B>, 0)|.$$

8. The image analysis apparatus according to claim 4, wherein where <R>, <G> and <B> are respective average values of R, G and B components in the first analysis object region, <R'>, <G'> and <B'> are respective average values of R, G and B components in the second analysis object region, Min(x, y) is a function that provides one that is not larger of x and y and α, β and γ(here, α>0, β>0, γ>0) are weight coefficients, the processor is configured to calculate the change degree as the following change rate:

$$\text{Change rate} = |\alpha \times \text{Min}(<R'> - <R>, 0) + \beta \times \text{Min}(<G'> - <G>, 0) + \gamma \times \text{Min}(<B'> - <B>, 0)| / |<R> + <G> + <B>|.$$

9. The image analysis apparatus according to claim 1, wherein the first and second images inputted to the processor are images picked up and acquired by an endoscope inserted in the subject.

10. The image analysis apparatus according to claim 9, wherein:
the first analysis object region and the second analysis object region are included in an image part of villi of an intestinal tract; and
the processor is configured to:
extract a predetermined number of parts of interest in the first image, the parts of interest each including an image part in which mucosal epithelium formed at a surface of the villi of the intestinal tract is shown as the first annular peripheral portion and an image part in which a site surrounded by the mucosal epithelium is shown as the first central portion having a color that is different from a color of the mucosal epithelium, and set the first central portion of each of the predetermined number of extracted parts of interest as the first analysis object region; and
extract a predetermined number of parts of interest in the second image, the parts of interest each including an image part in which mucosal epithelium formed at the surface of the villi of the intestinal tract is shown as the second annular peripheral portion and an image part in which the site surrounded by the mucosal epithelium is shown as the second central portion having a color that is different from a color of the mucosal epithelium, and set the second central portion of each of the predetermined number of extracted parts of interest as the second analysis object region.

11. An image analysis system comprising:
an endoscope to be inserted into a subject to pick up and acquire an image of the subject; and
an image analysis apparatus according to claim 1,
wherein the image acquired by the endoscope is inputted to the processor.

12. An image analysis apparatus operating method comprising:
inputting time-sequentially-acquired images of a subject, the time-sequentially-acquired images including a first image acquired at a first time and a second image acquired at a second time after the first time;
extracting first parts from the first image, each of the extracted first parts including a first annular peripheral portion and a first central portion surrounded by the first annular peripheral portion, the first central portion having a first color that is different from a second color of the first annular peripheral portion;
extracting second parts from the second image, each of the extracted second parts including a second annular peripheral portion and a second central portion surrounded by the second annular peripheral portion, the second central portion having a third color that is different from a fourth color of the second annular peripheral portion;
setting the first central portion of each of the extracted first parts as a first analysis object region;
setting the second central portion of each of the extracted second parts as a second analysis object region; and
calculating a brightness decrease degree of the second analysis object region relative to the first analysis object region, the second analysis object region having a brightness decreased relative to the first analysis object region.

\* \* \* \* \*